United States Patent [19]

Carmichael et al.

[11] Patent Number: 4,579,009
[45] Date of Patent: Apr. 1, 1986

[54] COUPLING FOR USE WITH MICROMANIPULATOR

[75] Inventors: Richard A. Carmichael, Keota; James C. Rogers, Iowa City, both of Iowa

[73] Assignee: Maplehurst Ova Transplants, Inc., Keota, Iowa

[21] Appl. No.: 685,039

[22] Filed: Dec. 21, 1984

[51] Int. Cl.⁴ .............................................. G01N 1/28
[52] U.S. Cl. .................... 73/863; 73/864.01; 285/90; 285/77; 285/298; 403/90; 403/362; 422/103
[58] Field of Search ................. 73/863, 864.01, 864.24, 73/864.25; 422/103, 104, 100; 279/16, 18; 285/90, 77, 78, 122, 298, 299; 403/299, 90, 137, 135, 122, 362; 350/252

[56] References Cited

U.S. PATENT DOCUMENTS

| 467,294 | 1/1892 | Mills | 279/16 |
|---|---|---|---|
| 1,300,428 | 4/1919 | Lowenstein | 279/16 X |
| 1,300,733 | 4/1919 | Keller | 279/16 X |
| 2,456,383 | 12/1948 | Collins | 403/90 X |
| 2,673,054 | 3/1954 | Slavik | 403/137 X |
| 3,252,330 | 5/1966 | Kling | 422/100 X |
| 3,262,452 | 7/1966 | Hardy et al. | |
| 3,457,922 | 7/1969 | Ray | |
| 3,588,025 | 6/1971 | Gersman | 403/90 X |
| 3,980,408 | 9/1976 | Jachmann | 403/362 X |
| 4,076,503 | 2/1978 | Atwood et al. | 422/100 |
| 4,128,456 | 12/1978 | Lee et al. | |
| 4,139,948 | 2/1979 | Tsuchiya et al. | |
| 4,203,683 | 5/1980 | Rogers | 403/135 X |
| 4,247,646 | 1/1981 | Berky et al. | |
| 4,360,028 | 11/1982 | Barbier et al. | |

FOREIGN PATENT DOCUMENTS

| 547982 | 10/1957 | Canada | 403/90 |
|---|---|---|---|
| 83914 | 8/1920 | Fed. Rep. of Germany | 403/90 |
| 334090 | 8/1930 | United Kingdom | 403/90 |
| 124069 | 3/1958 | U.S.S.R. | 422/100 |
| 979999 | 12/1982 | U.S.S.R. | 73/863 |

OTHER PUBLICATIONS

Leitz Micromanipulator brochure, date unknown but prior to 12-21-84, pertinent pages: 5-8.

*Primary Examiner*—Stewart J. Levy
*Assistant Examiner*—Tom Noland
*Attorney, Agent, or Firm*—Zarley, McKee, Thomte, Voorhees & Sease

[57] ABSTRACT

The coupling of the present invention is adapted for use with a micromanipulator and a pair of pipettes. The micromanipulator comprises a pair of elongated arms and linkage connected to the arms for moving the arms in a plurality of directions. The coupling includes a housing having an arm receptacle at one end and a pipette holding device at the opposite end. A ball and socket swivel is provided within the housing and comprises a movable socket member which is matingly engaged with a spherical ball. The ball is connected to the pipette holding device. A threaded bolt engages the movable socket member and is adapted to cam the socket member into frictional engagement with the ball so as to lock the ball and socket joint against movement.

10 Claims, 6 Drawing Figures

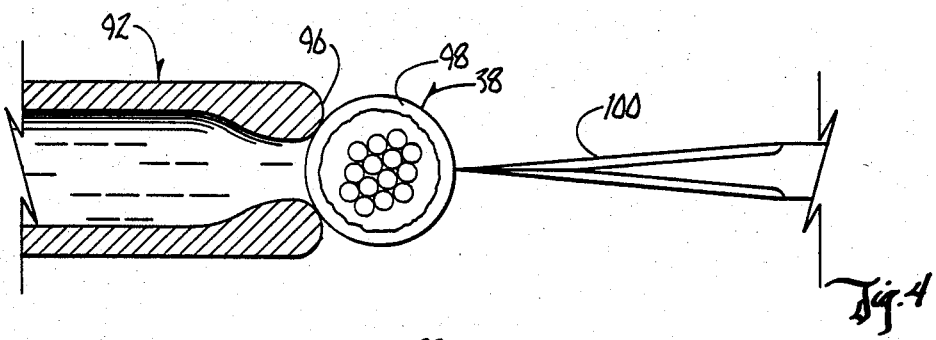
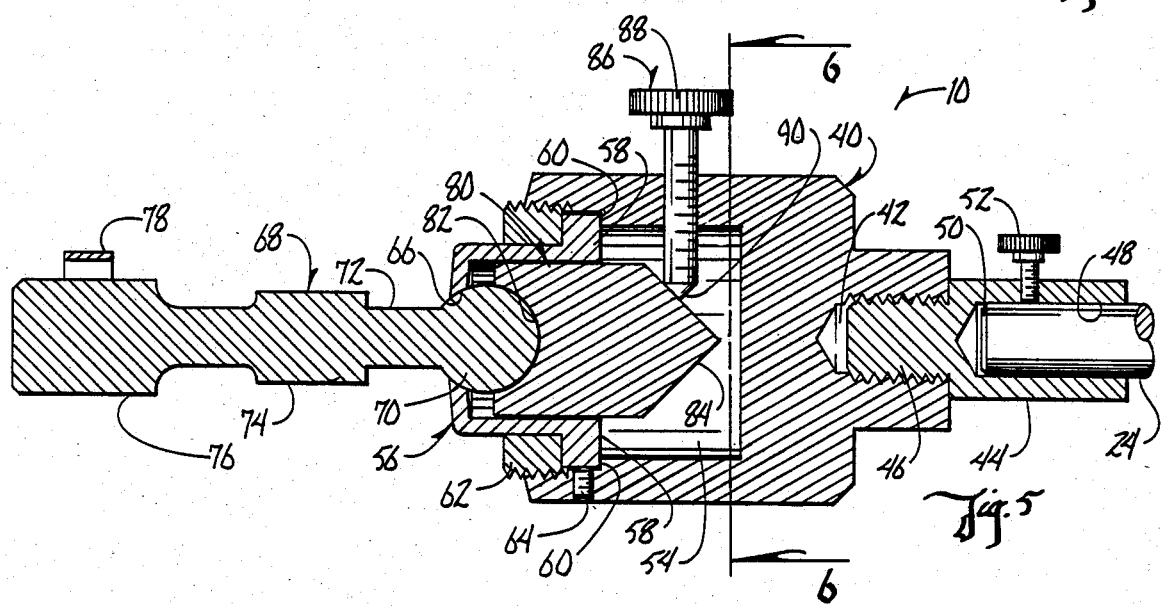
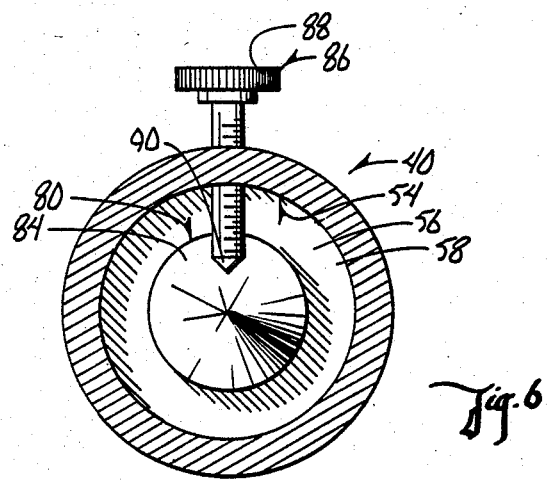

COUPLING FOR USE WITH MICROMANIPULATOR

BACKGROUND OF THE INVENTION

The present invention relates to a coupling adapted for use with a micromanipulator.

Micromanipulators are devices used in the field of cell physiology for the purpose of physically altering the cell structure of an embryo in its early stage of development. The micromanipulator includes arms which may be connected to instruments for physically altering the cell structure of the embryo. The manipulator permits small precise movements necessary in order to perform operations on the embryo.

One instrument which is attached to the micromanipulator is usually a pipette filled with water or other fluid. The pipette is used to hold the cell while it is being operated upon by an instrument. Another instrument held by the manipulator is often a knife which is adapted to cut the outer wall of the embryo, so as to permit the internal structure of the embryo to be altered. This work is usually accomplished under a microscope.

One disadvantage of present micromanipulators is the difficulty in attaching the pipette or other instrument to the arms of the manipulator in the proper position for operating on the embryo. This is particularly difficult when the embryo is contained within a Petri dish which requires that the angle and position of the instruments be precisely adjusted before commencing the operation.

Therefore, a primary object of the present invention is the provision of an improved coupling for use with a micromanipulator.

A further object of the present invention is the provision of a coupling which permits universal movement of the instrument holding device so that the position of the instrument can be adjusted prior to the operation on the embryo.

A further object of the present invention is the provision of a coupling which can be tightened so as to prevent any further movement of the coupling joint after it has been adjusted to the proper position.

A further object of the present invention is the provision of a coupling device which provides an extension of the arms of the micromanipulator.

A further object of the present invention is the provision of a coupling device which can be used in combination with numerous micromanipulators presently on the market.

A further object of the present invention is the provision of a coupling device which is economical to manufacture, durable in use and efficient in operation.

SUMMARY OF THE INVENTION

The present invention untilizes a coupling having a coupling housing. At one end of the coupling housing is a receptacle for receiving the distal end of one of the micromanipulator arms. At the opposite end of the housing is an instrument holding member for holding a pipette or other instrument.

A ball and socket swivel joint connects the instrument holding member to the housing. This ball and socket joint is contained within a cavity inside the coupling housing. A ball is contained within the housing and includes a shank extending through an opening in the coupling housing. Engaging the ball is a movable socket member also within the coupling housing. The socket member includes a cam surface which is engaged by a threaded bolt. The threaded bolt can be moved to cam against the cam surface of the socket member so as to cause the socket member to move into tight frictional engagement with the ball and thereby hold the ball against swiveling movement.

A clip is provided on the instrument holding member for retentively engaging the instrument. In operation, the instrument is clipped to the instrument holding member. The threaded bolt is then loosened so as to permit the ball and socket joint to swivel freely. The ball and socket joint is maneuvered to the desired position and the threaded bolt is tightened so as to hold the ball and socket joint against further movement.

The socket which engages the ball encompasses at least one-fourth of the surface of the ball, and preferably between one-fourth and one-half of the surface of the ball. This provides a large surface of engagement between the ball and the socket so that when the socket member is tightened against the ball it will provide strong, positive control of the ball, and will prevent the ball from moving.

BRIEF DESCRIPTION OF THE FIGURES OF THE DRAWINGS

FIG. 4 is an enlarged sectional view of the end of the pipette, the embryo being operated upon, and the cutting instrument for cutting the outer wall of the embryo.

FIG. 5 is an enlarged sectional view taken along line 5—5 of FIG. 3.

FIG. 6 is a sectional view taken along line 6—6 of FIG. 5.

DETAILED DESCRIPTION OF THE PREFERRED EMBODIMENT

Figure 1:
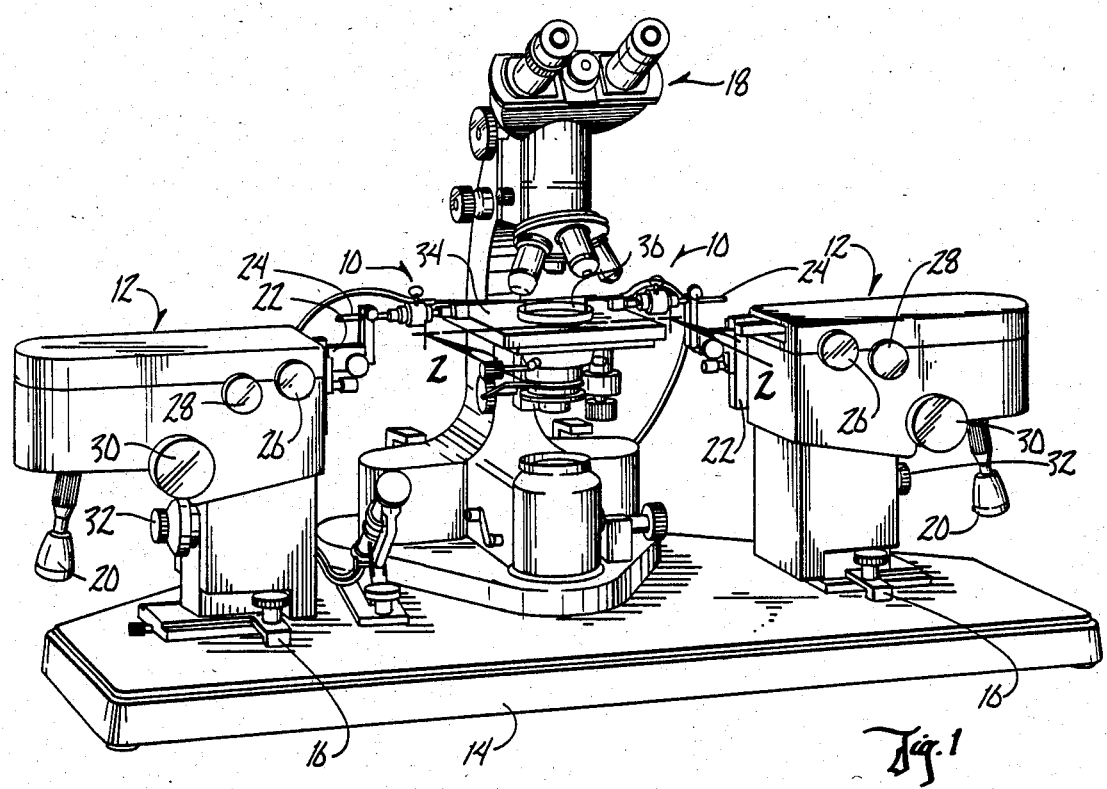
FIG. 1 is a perspective view of a micromanipulator utilizing the coupling of the present invention.

Referring to FIG. 1, the numeral 10 generally designates the coupling device of the present invention.

Two coupling devices 10 are shown in use with a pair of micromanipulator assemblies 12 which are mounted on a base plate 14 by means of a pair of clamps 16. Also mounted on base plate 14 is a microscope 18. Microscope 18 and micromanipulator assemblies 12 may differ from those shown in the drawings inasmuch as there are numerous various types of microscopes and micromanipulators currently commercially available.

Each micromanipulator assembly includes a handle 20 which operates to move a manipulator arm 22. Each manipulator arm 22 includes a short rod or shaft 24 which is adapted to be attached to the instruments performing the operation. Various adjustment knobs 26, 28, 30, 32 are provided on the micromanipulator for adjusting the movements provided by the micromanipulator.

The microscope 18 is of conventional construction and includes a platform 13 upon which is placed a Petri dish 36 which contains the embryo 38 (FIG. 4) upon which the operation is to be performed. Usually these embryos are in their earliest stage of development after fertilization.

The coupling 10 of the present invention includes a coupling housing 40 which includes a threaded bore 42 at one end thereof. Threaded within threaded bore is a receptacle 44 having a threaded end 46 and having a cylindrical bore 48 at the opposite end thereof. Bore 48 is sized to receive the distal end 50 of rod or shaft 24 of the manipulator assemblies 12. A threaded bolt 52 extends through the body of receptacle 44, and engages rod 24 to hold rod 24 within bore 48 of receptacle 44.

Housing 40 also includes a cavity 54 formed therein. Within cavity 54 is a bushing 56 having an annular flange 58. Flange 58 abuts against a shoulder 60 and is held tightly thereagainst by a threaded nut 62. A set screw 64 extends through housing 40 and also engages annular flange 58 to prevent any rotational movement of flange 58.

Bushing 56 includes an opening 66 therein. An instrument holding member 68 includes a ball 70 which is within cavity 54 and which has a diameter greater than the diameter of opening 66 so that ball 70 cannot be removed from cavity 54 through opening 66. Connected to ball 70 is a shank 72 which has a first square portion 74, and a second square portion 76. Attached to square portion 76 is a clamp 78 which is adapted to retentively hold an instrument for use in operating on the embryo 38.

Within cavity 54 is a socket member 80 which includes a socket 82 at one end and a cone shaped cam surface 84 at the opposite end. Socket member 80 is cylindrical at its forward end and is slidably fitted within the bushing 56 so that it can slide longitudinally toward and away from the ball 70.

A threaded bolt 86 having a handle 88 threadably extends through housing 40 and includes a lower end 90 which engages the cone shaped surface 84 of socket member 82.

When threaded bolt 86 is moved upwardly, it releases socket member 80 for longitudinal sliding movement within bushing 56. As threaded bolt 88 is threaded downwardly, it engages the cam surface 84 and causes the socket member 80 to move to the left as viewed in FIG. 5. This causes the socket 82 to engage ball 70 and as it is tightened against ball 70, it holds ball 70 against any swivel movement. The socket 82 engages greater than one-fourth of the surface of ball 70 so that the contact surface area between the ball 70 and socket 82 is sufficient to hold instrument holding member 68 against any further swivel movement.

In the operation, the coupling device 10 is attached to the rod 24 of manipulator 12 by inserting rod 24 into receptacle 44 and by tightening screw 52 down to retentively hold shaft 24 within the bore 48 of receptacle 44. Respective ones of the two coupling devices 10 are mounted to respective ones of the two micromanipulator assemblies 12 in this manner.

Figure 2:
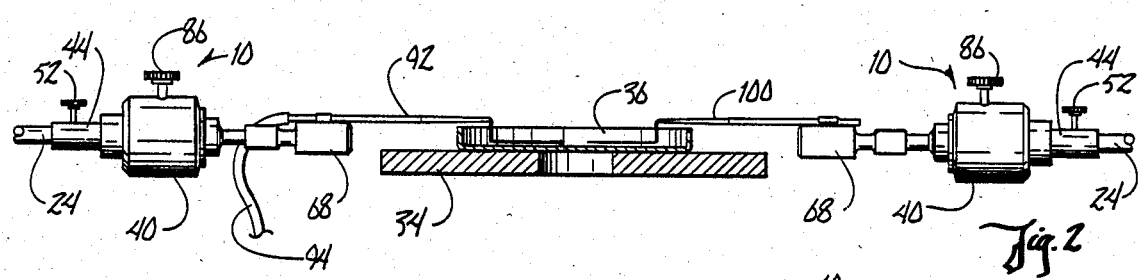
FIG. 2 is a sectional view taken along line 2—2 of FIG. 1.
Figure 3:
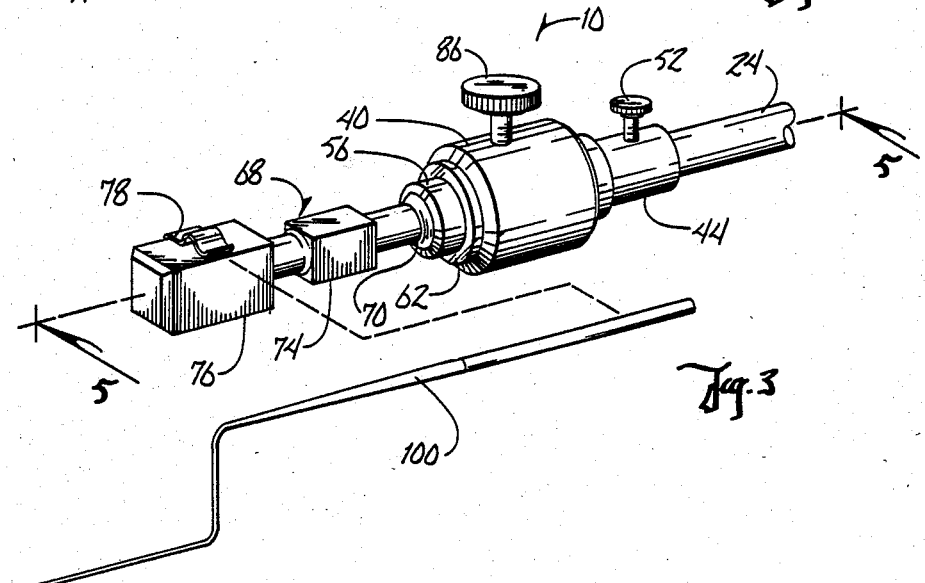
FIG. 3 is an enlarged detailed perspective view showing the coupling of the present invention.

Next a pipette 92 or other instrument is attached to one of the coupling members by means of clamp 78 as shown in FIG. 2. Pipette 92 is connected to a hose 94 which supplies fluid to the pipette 92. As shown in FIG. 4, pipette 92 includes a distal end 96 which is open. The fluid within pipette 92 engages the embryo 38, and then is placed under a very slight vacuum so as to hold embryo 98 against the distal end 96 of pipette 92. This results from the adhesive forces between the fluid within pipette 92 and the outer embryo wall 98.

Mounted to the other coupling member 10 is a knife or cutting instrument 100. After pipette 92 and cutting instrument 100 are attached by means of clip 78 to holding member 68, the screw 86 is loosened so as to permit universal swiveling movement of ball 70 with respect to socket 82. This permits the operator to position the pipette 92 and the cutting instrument 100 in the desired orientation within Petri dish 36. After the desired position of these two instruments is achieved, screws 86 are tightened down to hold the coupling 10 against any further swivel movement. The ball and socket joint provide a tight positive locking of the swivel movement so that no undesired swivel movement will occur.

The operator then manipulates handles 20 of the micromanipulators 12 so as to bring the knife 100 into engagement with the embryo wall 98 of embryo 38. It is thus possible to sever the embryo wall 98 and to alter the internal structure of the embryo so as to achieve the desired result.

The coupling of the present invention provides an improvement over prior coupling devices in that it permits the universal adjustment of the positions of the pipette and the knife prior to beginning the operation. In prior devices, this has been particularly difficult when the embryo is placed within a Petri dish which has vertical walls around the edge thereof. With the embryo at the bottom of the Petri dish, it is difficult to place the ends of the pipette 92 and the knife 100 in proper position for severing the wall 98 of the embryo.

Another advantage of the present invention is that the longitudinal axis of holding member 68 is a continuation of the longitudinal axis of rod 24 of the micromanipulator. Thus, the coupling member 10 provides a continuation of the rod 24.

Another advantage is obtained by the socket member 80. Socket member 80 engages at least one-fourth of the surface area of ball 70 so as to provide a strong, positive locking of the ball when screw 86 is tightened down.

Thus, it can be seen that the device accomplishes at least all of its stated objectives.

What is claimed is:

1. An improved coupling for use with a micromanipulator assembly and a pipette, said micromanipulator assembly comprising an elongated arm having a distal end, and means connected to said arm for moving said arm in a plurality of directions, said pipette comprising an elongated hollow tube having an outlet end and an inlet end, said improved coupling comprising:
   a coupling housing having a first end, and a second end, and having a cavity formed therein;
   said housing having an arm receptacle at said first end of said housing for detachably retentively receiving said arm of said micromanipulator assembly;
   a pipette holding member having clip means thereon for detachably retentively holding said pipette;
   swivel means mounting said holding member to said second end of said housing for permitting universal swiveling movement of said holding member with respect to said housing;
   said swivel means comprising a ball and a movable socket member within said housing, said ball being connected to said holding member, said socket member having a socket shaped to matingly fit said ball, said socket member being movable within said cavity of said housing from a release position permitting said ball to swivel universally with respect to said socket to a lock position wherein said socket frictionally engages said ball and holds said ball against movement with respect to said housing;
   control means engaging said socket member for causing said socket member to move between said release position and said lock position.

2. An improved coupling according to claim 1 wherein said socket member further comprises a cam surface, said control means engaging said cam surface for causing cammed movement of said socket member from said release position to said lock position.

3. An improved coupling according to claim 2 wherein said control means comprises an elongated threaded member having a first end outside said housing and a second end within the cavity of said housing, said threaded member extending through a threaded opening of said housing, handle means being connected to said first end of said threaded member, said second end of said threaded member frictionally engaging said cam surface of said socket member.

4. An improved coupling according to claim 3 wherein said socket member is movable in a first direction from said release to said lock position, and said threaded member is threadably movable within said threaded opening in a second direction for causing cammed movement of said socket member from said release to said lock positions, said first direction and said second directions being approximately perpendicular to one another.

5. An improved coupling according to claim 4 wherein said cam surface of said socket member is cone shaped around a cone axis which extends in said first direction and said socket faces in said first direction.

6. An improved coupling according to claim 1 wherein said socket has a concave shape which conforms to the shape of said ball and which frictionally engages at least one-fourth of the surface area of said ball when said socket member is in said lock position.

7. An improved coupling according to claim 1 wherein said receptacle is shaped to matingly receive said distal end of said arm of said micromanipulator assembly, thread screw means threadably extending into said coupling for engaging and holding said distal end within said receptacle.

8. An improved coupling according to claim 1 wherein said pipette holding member and said ball are rigidly connected to one another by shank means, said housing having an opening therein which is smaller than the diameter of said ball and which is sufficiently large to permit said shank means to extend therethrough, said ball being at least partially within said cavity and said shank means extending through said opening.

9. An improved coupling according to claim 8 wherein said receptacle is cylindrical, has a longitudinal cylindrical axis, said opening of said housing having a central axis which is parallel to said longitudinal cylindrical axis of said receptacle.

10. An improved coupling according to claim 9 wherein said central axis of said opening coincides with said cylindrical axis of said receptacle.

* * * * *